| United States Patent [19] | [11] Patent Number: 4,888,323 |
| Matsuda et al. | [45] Date of Patent: Dec. 19, 1989 |

[54] PERFUME COMPOSITION

[75] Inventors: Hiroyuki Matsuda; Takeshi Yamamoto, both of Tokyo, Japan

[73] Assignee: Takasago International Corporation, Tokyo, Japan

[21] Appl. No.: 209,396

[22] Filed: Jun. 21, 1988

[30] Foreign Application Priority Data

Jun. 22, 1987 [JP] Japan ................................ 62-153440

[51] Int. Cl.$^4$ .............................................. A61K 7/46
[52] U.S. Cl. ..................................................... 512/23
[58] Field of Search ........................... 568/376; 512/23

[56] References Cited

U.S. PATENT DOCUMENTS 2,582,743  1/1952  Bollmann et al. ..................... 512/23
4,751,214  6/1988  Gramlich et al. ..................... 512/23

OTHER PUBLICATIONS

Reid et al., J.A.C.S., vol. 72, pp. 5232–5236 (1950).
Allinger et al., J.A.C.S., vol. 83, pp. 944–945 (1961).
Servis et al., J.A.C.S., vol. 95, pp. 3392–3394 (1973).
Alvarey et al., Chem. Abst., vol. 104, #5252; (1980).

*Primary Examiner*—James H. Reamer
*Attorney, Agent, or Firm*—Sughrue, Mion, Zinn, Macpeak & Seas

[57] ABSTRACT

A perfume composition comprising 2,4-di-tert-butylcyclohexanone is disclosed. This perfume composition has a highly preferable and fresh scent and thus widely available in, for example, perfumes, cosmetics, hygienic products and medicines. The 2,4-di-tert-butylcyclohexanone, which may be in the form of either a cis-isomer, a trans-isomer or a mixture thereof, is highly safe and stable.

7 Claims, No Drawings

PERFUME COMPOSITION

FIELD OF THE INVENTION This invention relates to a perfume composition. More particularly, it relates to a perfume composition which comprises 2,4-di-tert-butylcyclohexanone of the following formula (I):

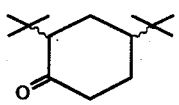

(I)

The perfume composition of the present invention can be effectively applied to, for example, perfumes, cosmetics, hygienic products and medicines.

BACKGROUND OF THE INVENTION 2,4-Di-tert-butylcyclohexanone is described in the following references. However these references have reported this compound from the viewpoints of reaction mechanism, stereochemistry or physicochemistry. Thus there has been no report on the scent of this compound. Further it has been never known that the 2,4-di-tert-butylcyclohexanone is available as a perfume.

REFERENCES: *An. Quim.*, Ser. C 1985, 81 (1), 41–3 (*Chemical Abstracts*, 104, 5252f (1986)), *Recl. Trav. Chim. PaVs-Bas*, 1974, 93 (4), 938 (*Chemical Abstracts*, 81, 77355z (1974)), *J. Am. Chem. Soc.*, 1973, 95 (10), 3392–4 (*Chemical Abstracts*, 79, 31383n (1973)), *Bull. Soc. Chim. Fr.*, 1966 (12), 3881-8 (*Chemical Abstracts*, 67, 21473e (1967)), *Bull. Soc. Chim. Fr.*, 1966 (12), 3888-95 (*Chemical Abstracts*, 67, 21474f (1967)), *J. Am. Chem. Soc.*, 83, 994–5 (1961), (*Chemical Abstracts*, 55, 15368), *J. Am. Chem. Soc.*, 72, 5232, 5235 (1950) and *J. Am. Chem. Soc.*, 71, 3798 (1949). .

Examples of known compounds, which are structurally similar to the compound of the present invention and have been used as a perfume, include 2-tert-butylcyclohexanon of the following formula (II) and 4-tert-butylcyclohexanone of the following formula (III), each containing ten carbon atoms (cf. S. Arctandar, *Perfume and Flavor Chemicals*, Montclair, (1969), Monograph Nos. 435 and 436).

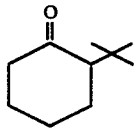

(II)

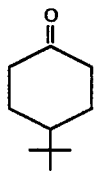

(III)

Although the compound (II) has a woody and camphoraceous scent of high diffusibility, the application range thereof as a perfume is considerably limited. On the other hand, the compound (III) has a powerful, dry and camphoraceous scent, slightly similar to that of mint, with a woody, cedarn and patchouli-like undertone and is employed as a modifier for patchouli in, for example, soaps and detergents.

Recent diversification of perfumes and cosmetics has increased the demand for a novel scent. Therefore it has been required to develop a perfume which has a mild and unique scent together with high safety and excellent stability. Thus it has been attempted to combine various known perfume materials at various ratios to thereby develop perfumes closely similar to natural ones. However there are few perfume materials simultaneously satisfying the above requirements, i.e., a fresh and natural scent, high safety and excellent stability, in particular, available at a low price.

SUMMARY OF THE INVENTION

Under these circumstances, the present inventors have investigated the following derivatives (V) to (IX) of 2,4-di-tert-butylphenol (IV) which is available at a low price.

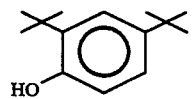

(IV)

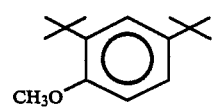

(V)

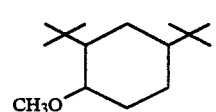

(VI)

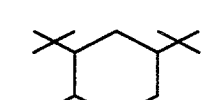

(VII)

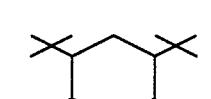

(VIII)

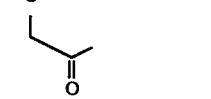

(IX)

The compound (V) has a slight, powdery and anise-like scent; the compound (VI) has an extremely slight and anise-like scent; the compound (VII) has a slight, camphoraceous, floral and violet-like scent; the compound (VIII) is almost odorless and has an extremely slight, fatty, rose and woody scent; and the compound (IX) is almost odorless and has an extremely slight, floral and woody scent. Thus the scent characteristics of these compounds other than the 2,4-di-tert-butylcyclohexanone (I) used in the present invention are not remarkable. Namely, the compound (I) alone exhibits a mild, soft, floral woody and violet-like scent and is highly safe and stable. Therefore the present inventors have found that the compound (I) is useful as a novel perfume material, thus completing the present invention.

Accordingly the present invention relates to a perfume composition comprising 2,4-i-tert-butylcyclohexanone.

DETAILED DESCRIPTION OF THE INVENTION

The 2,4-di-tert-butylcyclohexanone can be synthesized, for example, by the following manner. 2,4-Di-tert-butylphenol (IV), which is commercially available at a low price, is hydrogenated by using a nickel catalyst to give 2,4-di-tert-butylcyclohexanol (VII). Then the compound (VII) is oxidized to give the aimed compound (I). The hydrogenation of the compound (IV) can be readily carried out without using any solvent or by using an alcohol such as methanol or a hydrocarbon such as hexane at a temperature of approximately 140° to 230° C. for approximately 3 to 24 hours. Examples of the nickel catalyst include Raney nickel and stabilized nickel. This nickel catalyst can be appropriately used in an amount of 0.01 to 5% based on the compound (IV). The oxidation of the compound (VII) into the compound (I) can be carried out by using a copper/chromium or copper/zinc dehydrogenation catalyst in the absence of any solvent at a temperature of approximately 150° to 250° C. for approximately 3 to 20 hours. The catalyst can be appropriately employed in an amount of approximately 0.1 to 10% by weight based on the compound (VII). Alternatively the compound (VII) can be readily oxidized by a conventional method for oxidizing a secondary alcohol into a ketone, such as Jones oxidation, Oppenauer oxidation, manganese dioxide oxidation or chromic acid oxidation.

Furthermore the 2,4-di-tert-butylcyclohexanone (I) can be synthesized in a single step at a high yield by selectively hydrogenating 2,4-tert-butylphenol (IV) with two moles of hydrogen by using a noble metal catalyst such as palladium. The hydrogenation of the compound (IV) can be carried out in the absence of any solvent at a temperature of approximately 100° to 230° C. for approximately 3 to 20 hours. Examples of the catalyst include noble metal catalysts such as palladium black, palladium carbon, palladium alumina, ruthenium, ruthenium carbon, rhodium and rhodium alumina. This catalyst can be appropriately employed in an amount of approximately 0.001 to 5% based on the compound (IV).

The 2,4-di-tert-butylcyclohexanone (I) thus prepared comprises two isomers, i.e., cis-isomer (I-A) and trans-isomer (I-B).

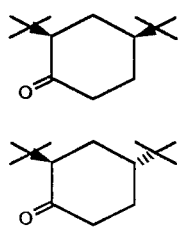

(I-A)

(I-B)

The 2,4-di-tert-butylcyclohexanone (I) has a soft, floral, woody, voilet-like and intense scent. The compound (I) containing a larger amount of the cis-isomer (I-A) shows a highly diffusible, gorgeous, cyclamen-like and floral scent. On the other hand, the compound (I) containing a larger amount of the trans-isomer (I-B) has a powerful, orris-like and woody scent. The safeties and stabilities of the compounds (I), (I-A) and (I-B), as a perfume cosmetic, are evaluated by sensitivity, primary skin irritation, phototoxicity and mutagenicity tests. Consequently none of these compounds show a positive result in any test, which proves that these compounds are highly safe. Further soaps are perfumed with these compounds and then exposed to UV light to thereby examine color change. Consequently no positive result is observed. Furthermore the perfume characteristics of each compound shows no change under specialized conditions, for example, in the presence of a hypochlorous acid bleaching agent. Thus it is found that these compounds (I), (I-A) and (I-B) are highly stable.

The 2,4-di-tert-butylcyclohexanone to be used in the present invention, in the form of either of a mixture of cis- and trans-isomers or each single isomer, is highly compatible with, for example, various synthetic perfumes, natural perfumes, synthetic essential oils and natural essential oils and thus available in the preparation of a novel perfume composition. When the 2,4 di-tert-butylcyclohexanone is blended with, for example, a synthetic essential oil such as lemon oil, orris oil, lavender oil or geranium oil, a mild and fresh scent inherently shown in a natural essential oil is imparted to the synthetic essential oil. Further it is highly compatible with citrus essential oils such as orange, lime, lemon and grapefruit oils, or natural essential oils such as sandalwood oil, vetiver oil, jasmin oil, violet leaf oil, lavender oil, rose oil, citronella oil, lavandine oil and geranium oil and makes the characteristics of each essential oil further remarkable. Thus the 2,4-di-tert-butylcyclohexanone is available in the preparation of a perfume composition having a mild, fresh and highly preferable scent. The amount of the 2,4-di-tert-butylcyclohexanone blended varies depending on the purpose and type of the perfume composition. Generally speaking, it can be employed in an amount ranging from approximately 0.01 to 50% by weight.

Thus the present invention makes it possible to provide an agent for imparting or enriching a mild, fresh and highly preferable scent which comprises 2,4-di-tert-butylcyclohexanone, as well as fragrance products, cosmetics, hygienic products, medicines, paints, etc. containing the above compound as a perfume ingredient. That is to say, an appropriate amount of the perfume composition of the present invention can be incorporated into, for example, cosmetics and toiletries, such as fragrances (e.g., toilet water, colognes and perfumes), hair care products (e.g., conditioners, hair sprays and shampoos), makeup products (e.g., face powders and lipsticks), nail care products, oral care products (e.g., mouthwashes and lip treatments), skin care products, and other products (e.g., bar and liquid soaps, deodorants and antiperspirants, depilatories, feminine hygiene deodorants, miscellaneous products and shaving products); households and cleansing products, such as soaps and detergents (e.g., laundry detergents), laundry additives, specialty cleaners, deodorizers and disinfectants (e.g., air fresheners, disinfectans and room aromatics), polishes, waxes, and paints; and others, such as additives for facilitating the administration of medicine, in order to impart the unique scent therto and to elevate the commercial value thereof.

To further illustrate the present invention, the following Synthetic Examples, Test Example and Examples will be given.

SYNTHETIC EXAMPLE 1

Synthesis of 2,4-di-tert-butylcyclohexanone (i)

300 g of 2,4-di-tert-butylphenol and 3.0 g of 5% palladium-carbon catalyst were introduced into a 500 ml autoclave and stirred therein at a reaction temperature of 180° C. under a hydrogen pressure of 20 kg/cm². After approximately ten hours, the absorption of the theoretical amount (2.9 moles) of hydrogen was confirmed. Then the reaction mixture was cooled to room temperature and the catalyst was filtered off. 218 g of the crude 2,4-di-tert-butylcyclohexanone thus obtained was distilled under reduced pressure in a Helipack packing column of a number of theoretical plates of 5 to give 245 g of a colorless and transparent 2,4-di-tert-butylcyclohexanone (I) fraction (b.p.: 93° to 94° C./3 mm Hg). It was confirmed by gas chromatography that this product was a mixture of cisisomer (I-A) and trans-isomer (I-B) at a ratio of 83:17. The physical properties of this product were as follows:

specific gravity (20°/20° C.): 0.8971 and
refractive index (20° C.): 1.4622.

This fraction was repeatedly rectified with a Helipack packing precision distillation column of a number of theoretical plates of 50, to separate the product into the colorless and transparent cis isomer (I-A) (b.p.: 93.1° C./3 mm Hg) and trans-isomer (I-B) (b.p.: 94.5° C./3 mm Hg).

The spectroscopic data of the compound (I-A) were as follows:

mass spectrum (m/e):
29, 43, 57, 70, 83, 97, 111, 125, 139, 154, 167, 177, 195 and 210;

infrared absorption spectrum ($cm^{-1}$):
2955, 2910, 2870, 1715, 1482, 1470, 1365, 1230 and 1135; and NMR spectrum (400 megacycle proton NMR) (ppm):
0.92 (9H, s), 0.99 (9H, s), 1.25 (1H, m), 1.42 to 1.55 (2H, m), 2.02 to 2.08 (1H, m), 2.11 to 2.20 (2H, m) and 2.28 to 2.32 (2H, m).

The spectroscopic data of the compound (I-B) were as follows:

mass spectrum (m/e):
29, 41, 57, 70, 83, 97, 111, 125, 139, 154, 177, 195 and 210;

infrared absorption spectrum ($cm^{-1}$):
2953, 2903, 2870, 1718, 1470, 1396, 1363, 1242, 1220 and 1050; and NMR spectrum (400 megacycle proton NMR) (ppm):
0.91 (9H, s), 1.02 (9H, s), 1.45 to 1.61 (2H, m), 1.66 to 1.74 (1H, m), 1.81 to 1.93 (2H, m), 2.15 to 2.26 (2H, m) and 2.36 to 2.43 (1H, m).

SYNTHETIC EXAMPLE 2

Synthesis of 2,4-di-tert-butylcyclohexanol 575 g (2.79 moles) of 2,4-di-dert-butylphenol and 17.25 g of Raney nickel were introduced into a 1 l autoclave and stirred therein at a reaction temperature of 200° C. under a hydrogen pressure of 50 kg/cm². After approximately 20 hours, the absorption of the theoretical amount (8.4 moles) of hydrogen was confirmed. Then the reaction mixture was cooled to 80° C. and the catalyst was filtered off. 573 g of the crude 2,4-di-tert-butylcyclohexanol thus obtained was rectified in a Helipack packing column of a number of theoretical plates of 5 to give 525.3 g of 2,4-di tert-butylcyclohexanol (b.p.: 104 to 105° C/6 mm Hg). This product was in the form of white crystal (m.p.: 99° to 100° C.) and the cis/trans ratio thereof, determined by gas chromatography, was 94/6.

SYNTHETIC EXAMPLE 3

Synthesis of 2,4-d-tert-butylcyclohexanone (ii)

200 g (0.944 mole) of the 2,4-di-tert-butylcyclohexanol as prepared in Synthetic Example 2 and 2.0 g of a copper/chromium catalyst were introduced into a 500 ml four-necked flask and vigorously stirred therein at a temperature of 215° to 220° C. under a reduced pressure of 200 to 300 mmHg. This dehydrogenation procedure was carried out for 15 hours. After completion of the reaction, the heating and stirring were ceased and the reaction mixture was cooled to room temperature. Then the catalyst was filtered off. Thus 194 g of crude 2,4-di-tert-butylcyclohexanone having a cis/trans ratio of 81/19 was obtained. This product was rectified under reduced pressure in a Helipack packing column of a number of theoretical plates of 5 to give 158 g of 2,4-di-tert-butylcyclohexanone (b.p.: 93° to 94° C./3 mm Hg). This product had a cis/trans ratio of 85/15.

SYNTHETIC EXAMPLE 4

Synthesis of 2,4-d-tert-butylcyclohexanone (iii)

200 g (0.944 mole) of the 2,4-di-tert-butylcyclohexanol as prepared in Synthetic Example 2 and 2 l of acetone were introduced into a 3 l reactor. Then 320 g of a Jones reagent was added dropwise thereto under ice-cooling at 5° C. over 1.5 hour. After completion of the reaction, isopropyl alcohol was added to the reaction mixture until the brown color of the excessive reagent disappeared. Then the reaction mixture was allowed to stand. After separating the acetone reaction solution, the acetone solution was neutralized with sodium carbonate. Then the solution was filtered and the acetone was distilled off under reduced pressure to give 199 g of crude 2,4 di-tert butylcyclohexanone. This product had a cis/trans ratio of 92/8. It was subjected to precision distillation in a Helipack packing column of a number of theoretical plates of 5 to give 160 g of 2,4 di-tert-butyl cyclohexanone (b.p.: 93.5 to 94° C./3 mm Hg). The cis/trans ratio of this product was 94/6.

TEST EXAMPLE

Perfuming of soap and stability test

Soaps were perfumed with 1% portions of the 2,4-di-tert-butylcyclohexanone (I) having a cis/trans ratio of 83/17 as prepared in Synthetic Example 1 and the isomers (I-A) and (I-B) isolated therefrom. Each soap was sealed in a glass container and stored in a thermostat at 40° C for three months. Then changes in the scent were evaluated by five panelists. As a result, every soap exhibited no decomposition odor and no change was observed in the scent thereof. These soaps were exposed to sunlight at room temperature for one month. As a result, no soap showed any discoloration.

EXAMPLE 1

Sodium hypochlorite bleaching composition

A liquid bleaching composition was prepared according to the following formulation. Formulation:

| | (% by weight) |
|---|---|
| sodium hypochlorite | 5.0 |
| sodium dodecyl ether sulfate (2 mole-ethylene oxide adduct) | 2.0 |
| sodium 2-ethylhexyl sulfate | 2.0 |
| sodium hydroxide | 1.0 |
| 2,4-di-tert-butylcyclohexanone (I) (prepared in Synthetic Example 1) | 0.2 |
| water | balance |

A masking test on the irritating odor characteristic to a bleaching agent of this composition was effected by employing five panelists. As a result, no panelist felt any irritating odor, which indicated that the irritating odor was completely masked by the compound of the present invention. This liquid bleaching agent was sealed in a polyethylene container and stored in a thermostat at 40° C. for one month. Then no change was observed in the odor of this composition. Further soiled towels were washed by using the liquid bleaching composition. As a result, these towels were completely bleached and imparted a comfortable, soft, floral woody and violet-like scent.

EXAMPLE 2

Perfume Composition

A perfume composition for soap was prepared according to the following formulation. Formulation:

| | (part by weight) |
|---|---|
| 2,6-dimethyl-7-octen-2-yl ethyl ether | 120 |
| lemon oil | 80 |
| lime oil | 40 |
| citral | 170 |
| 2-methyl-p-tert-butylcinnamic aldehyde | 150 |
| patchouli oil | 70 |
| lavandin oil | 20 |
| olibanum resin | 40 |
| aldehyde C-11 | 4 |
| 1,3,4,6,7,8-hexahydro-4,6,6,7,8,8-hexamethylcyclopenta-γ-2-benzopyran (as 50% solution in benzyl benzoate) | 50 |
| acetyl cedrene | 66 |
| phenylethyl alcohol | 70 |
| dihydroterpinyl acetate | 70 |
| methyl ionone | 50 |
| | 1000 |

66 parts by weight of the acetyl cederne in the above formulation was replaced with the trans-isomer (I-B) of 2,4-di-tert-butylcyclohexanone as obtained in Synthetic Example 1 to give another perfume composition. These two compositions were subjected to a preference test by employing five panelists. As a result, all panelists preferred the composition comprising the compound (I-B) and evaluated the same as a suitable perfume composition for soap exhibiting a fresh and well-balanced scent.

EXAMPLE 3

Perfume Composition

A perfume composition for men's fragrance was prepared according to the following formulation. Formulation:

| | (part by weight) |
|---|---|
| lime oil | 120 |
| 2,6-dimethylheptan-2-yl ethyl ether | 40 |

-continued

| | (part by weight) |
|---|---|
| phenylacetaldehyde | 20 |
| styrallyl acetate | 30 |
| 2-acetyl-2,3,8,8-tetramethyloctalene | 100 |
| eugenol | 60 |
| patchouli oil | 120 |
| cis-3-hexenyl salicylate | 120 |
| petigrain oil | 40 |
| mandarin oil | 80 |
| clary sage oil | 40 |
| 1,3,4,6,7,8-hexahydro-4,6,6,7,8,8-hexamethylcyclopenta-γ-2-benzopyran (as 50% solution in benzyl benzoate) | 230 |
| | 1000 |

960 parts by weight of the above perfume composition was blended with 40 parts by weight of the cis-isomer of 2,4-di-tert-butylcyclohexanone (I-A) as obtained in Synthetic Example 1 to give another composition. These two perfume compositions were subjected to a preference test by employing ten panelists. As a result, nine panelists among ten preferred the composition containing the compound (I-A) which had a mild, fresh and preferable scent.

EXAMPLE 4

Perfume Composition

A rose oil type composition was prepared according to the following formulation. Formulation:

| | (part by weight) |
|---|---|
| phenylethyl alcohol | 200 |
| geraniol | 50 |
| heliotropin | 20 |
| citronellol | 10 |
| nerol | 100 |
| hydroxycitronellal | 30 |
| methylphenylcarbinyl acetate | 25 |
| geranium oil | 10 |
| linalool | 30 |
| benzyl acetate | 35 |
| benzyl alcohol | 20 |
| rosephenone | 10 |
| rhodinol | 280 |
| rose oil | 10 |
| β-ionone | 50 |
| benzyl salicylate | 40 |
| cyclopentadecanolide | 30 |
| guaiacwood oil | 50 |
| | 1000 |

940 parts by weight of the above perfume composition was blended with 60 parts by weight of the 2,4-di-tert-butylcyclohexanone (I) as prepared in Synthetic Example 3 having a cis/trans ratio of 81/19 to give another perfume composition. These two perfume compositions were subjected to a preference test by employing five panelists. As a result, all panelists preferred the novel composition comprising the compound (I) which exhibited a more natural and fresh scent.

EXAMPLE 5

Perfume Composition

A highly preferably novel muguet type perfume composition for detergent powders was prepared according to the following formulation.

Formulation

| | (part by weight) |
|---|---|
| aldehyde C-9 (as 10% solution in diethyl phthalate) | 4 |
| 2-methylundecanal-1 (as 10% solution in diethyl phthalate) | 12 |
| aldehyde C-10 (as 10% solution in diethyl phthalate) | 4 |
| patchouli oil | 2.5 |
| cyclamen aldehyde | 6.5 |
| p-tert-butyl-2-methylhydroxycinnamic aldehyde | 10.5 |
| phenylethyl alcohol | 247 |
| citronellol | 130 |
| citronellal | 1 |
| dihydromyrcenol | 4 |
| eucalyptus oil | 1 |
| orange oil | 25 |
| lavandin oil | 7 |
| phenyl isobutyrate | 20 |
| phenylethyl phenylacetate | 33 |
| α-n-hexyl cinnamic aldehyde | 105 |
| 1,3,4,6,7,8-hexahydro-4,6,6,7,8,8-hexamethylcyclopenta-γ-2-benzopyran (as 50% solution in benzyl benzoate) | 15 |
| dodecahydro-3a,6,9a-tetramethyl-(2,1-b)-furan (as 5% solution in dipropylene glycol) | 15 |
| tetrahydrolinalool | 20 |
| isobornylcyclohexanol | 33 |
| allyl cyclohexanepropionate | 5 |
| 2,4-di-tert-butylcyclohexanone (I) (obtained in Synthetic Example 4) | 90 |
| | 1000 |

As described above, the present invention provides a perfume composition comprising 2,4-di-tert-butylcyclohexanone having a mild, soft, floral woody and voilet-like scent which is highly preferable and fresh. The perfume composition of the present invention is widely available in cosmetics and toiletries, households and cleansing products, and medicines.

While the invention has been described in detail and with reference to specific embodiments thereof, it will be apparent to one skilled in the art that various changes and modifications can be made therein without departing from the spirit and scope thereof.

What is claimed is:

1. A perfume composition which contains 2,4-di-tert-butylcyclohexanone.

2. A perfume composition as in claim 1, wherein said 2,4-di-tert-butylcyclohexanone is in the form of a mixture of cis- and trans-isomers.

3. A perfume composition as in claim 1, wherein said 2,4-di-tert-butylcyclohexanone is in the form of a cis-isomer.

4. A perfume composition as in claim 1, wherein said 2,4-di-tert-butylcyclohexanone is in the form of a trans-isomer.

5. A perfume composition as in claim 1, which contains 2,4-di-tert-butylcyclohexanone in an amount of from approximately 0.01 to 50% by weight based on the total composition.

6. A composition containing from approximately 0.01 to 50% by weight, based on the total composition, of 2,4-di-tert-butylcyclohexanone and an adjuvant therefor selected from synthetic perfumes, natural perfumes, synthetic essential oils and natural essential oils.

7. A process for imparting or enriching the scent of a perfume comprising the step of adding to said perfume from approximately 0.01 to 50% by weight of 2,4-di-tert-butylcyclohexanone.

* * * * *